United States Patent [19]

Yevich

[11] Patent Number: 4,784,998

[45] Date of Patent: Nov. 15, 1988

[54] 1,3,4-OXADIAZOLE PYSCHOTROPIC COMPOUNDS

[75] Inventor: Joseph P. Yevich, Southington, Conn.

[73] Assignee: Bristol-Myers Company, New York, N.Y.

[21] Appl. No.: 34,372

[22] Filed: Apr. 6, 1987

[51] Int. Cl.$^4$ .................. A61K 31/495; C07D 271/10; C07D 241/04
[52] U.S. Cl. .................................. 514/252; 544/366
[58] Field of Search ........................ 544/366; 514/252

[56] References Cited

U.S. PATENT DOCUMENTS

| | | |
|---|---|---|
| 3,381,009 | 4/1968 | Palozzo et al. ...................... 544/362 |
| 3,857,845 | 12/1974 | Palozzo ............................... 544/366 |
| 4,338,317 | 7/1982 | Temple et al. ...................... 544/366 |
| 4,367,335 | 1/1983 | Temple et al. ...................... 544/364 |
| 4,456,756 | 6/1984 | Temple et al. ...................... 544/364 |
| 4,487,773 | 12/1984 | Temple et al. ...................... 544/295 |

Primary Examiner—Donald G. Daus
Assistant Examiner—Cecilia Shen
Attorney, Agent, or Firm—Richard P. Ryan

[57] ABSTRACT

Psychotropic 1,3,4-oxadiazole compounds and their use as tranquilizers, analgesics and antidepressants.

10 Claims, No Drawings

1,3,4-OXADIAZOLE PYSCHOTROPIC COMPOUNDS

BACKGROUND OF THE INVENTION

The present invention relates to 1,3,4-oxadiazole heterocyclic carbon compounds and to their preparation and use. More particularly, the invention relates to 1,3,4-oxadiazoles substituted in the 2-position with 3-chlorophenylpiperazinylalkyl moieties and their therapeutic use in treating depression.

3-chlorophenylpiperazinylalkyl derivatives of certain heterocycles have been previously disclosed as having psychotropic activity and specifically being of use in the treatment of depression. These art compounds, as well as those of the present invention, can be represented structurally as depicted below.

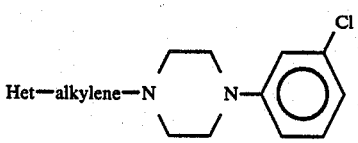

In this structure Het denotes certain heterocyclic moieties and it is the nature of these that distinguishes the art compounds from those of the instant invention as well as from each other. Temple and Lobeck in U.S. Pat. No. 4,487,773 disclose and claim a series of compounds (1) depicted structurally below.

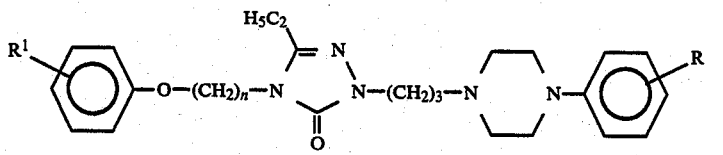

wherein R is halogen or alkoxy; n is 2–4; and $R^1$ is hydrogen, halogen or alkoxy. These compounds have antidepressant activity.

U.S. Pat. No. 3,857,845 to G. Palazzo describes the antidepressant compound (2) commonly called etoperidone. The structure for etoperidone is depicted below.

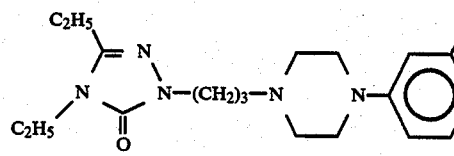

U.S. 3,381,009 to G. Palazzo, et al., discloses a related series of 1,2,4-triazolo [4.3-a] pyridines of which one compound, commonly known as trazodone, is an effective antidepressent in man. The structure for trazodone (3) is shown below.

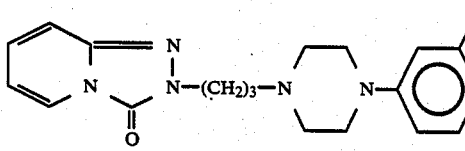

Temple and Yeager in U.S. Pat. No. 4,367,335 and U.S. Pat. No. 4,456,756 disclose and claim a series of compounds (4) with psychotropic properties whose structure is depicted below.

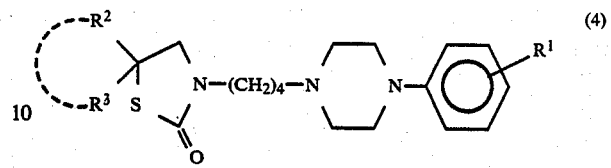

wherein $R^1$ is, inter alia, halogen.

None of the aforementioned references disclose or suggest piperazine derivatives containing the 1,3,4-oxadiazole heterocyclic component of the subject compounds of this invention.

SUMMARY AND DETAILED DESCRIPTION OF THE INVENTION

In its broadest aspect the present invention is concerned with compounds of Formula I and their acid addition salts and/or solvates.

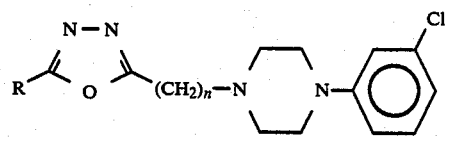

In the foregoing structrual formula, R can be a $C_{1-4}$ alkyl group, trifluoromethyl or pentafluoroethyl group; and n is the integer 3 or 4. A preferred class of compounds is those wherein n is 3 and R is methyl or trifluoromethyl.

As indicated, the present invention also pertains to the pharmaceutically acceptable acid addition salts of the compounds of Formula I. Such salts include those derived from organic and inorganic acids such as, without limitation, hydrochloric acid, hydrobromic acid, phosphoric acid, sulfuric acid, methanesulfonic acid, acetic acid, tartaric acid, lactic acid, succinic acid, citric acid, maleic acid, sorbic acid, aconitic acid, salicylic acid, phthalic acid, embonic acid, enanthic acid, and the like.

The compounds of the present invention can be produced by facile modification of standard synthetic methods for preparation of 1,3,4-oxadiazole analogs. The method of choice for synthesis of compounds of the present invention is outlined in Scheme 1, wherein R and n are defined above.

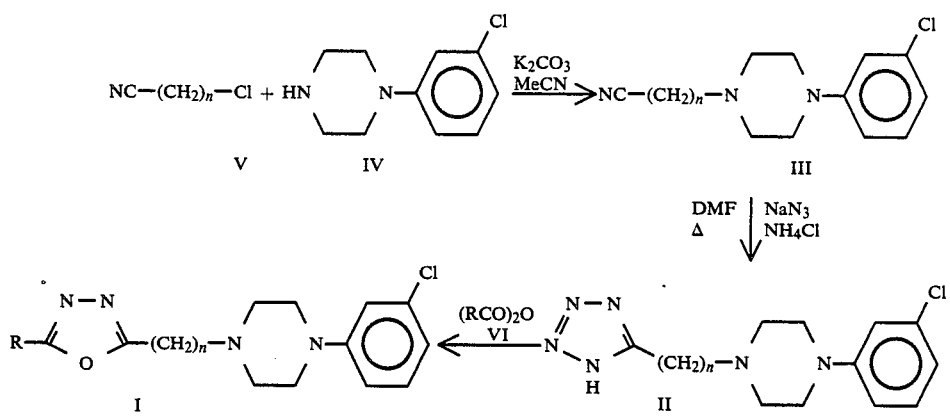

As shown in Scheme I alkylation of 3-chlorophenyl-piperazine (IV) with chloroalkylnitriles (V) gives the intermediate nitrile (III). Treatment of III with sodium azide and ammonium chloride in dimethylformamide affords the intermediate tetrazoles (II). The tetrazoles are converted to the desired 1,3,4-oxadiazole products (I) by reaction with the appropriate anhydride (VI).

The formula I compounds are useful pharmacologic agents with psychotropic properties. In this regard they exhibit selective central nervous system effects indicative of general tranquilizing action as well as analgesic and antidepressant actions. These activities are measured according to conventional in vivo test systems such as those listed below.

| In Vivo test | Description |
| --- | --- |
| 1. Suppression of conditioned avoidance response (CAR) | This test is indicative of general tranquilizing action; cf: Albert, et al., Pharmacologist, 4/152 (1962). |
| 2. Prevention of phenylquinone writhing | This test detects agents capable of preventing the phenylquinone writhing syndrome in mice. Analgesics, tranquilizers and anxiolytics are among such agents; cf: Henderskot, et al., J. Pharmacol. Expt'l Therapeutics, 125: 237 (1959). |
| 3. Induction of catalepsy | This test determines the cataleptogenic potential of centrally acting compounds; cf: Costall, et al., Psychopharmacologia, 34: 233–241 (1974). |
| 4. Inhibition of Pernicious Preening | This test detects potential psychotropic or analgetic agents: cf: Wilfron, et al., Fed. Proc. 19: 21 (1960). |
| 5. Prevention of reserpine-induced ptosis | This test is indicative of antidepressant action; cf: Niemegeers, Industrial Pharmacology, Vol. 2 Antidepressants, Ed. by S. Fielding and H. Lal, pp. 73–98, Futura, New York, NY, (1975) |

In these tests, the compounds of the present invention suppressed CAR in the rat, prevented phenylquinone writhing in the mouse, did not cause catalepsy (an undesirable side-effect), inhibited pernicious preening and reserpine-ptosis.

Another aspect of the instant invention concerns a method for inducing desired psychotropic action in a mammal requiring such treatment. In this regard the compounds of the instant invention can effect general tranquilizing action as well as analgesic and antidepressant actions in the mammal to be treated. The method for treatment of the mammal comprises administering systemically to said mammal a therapeutically effective amount of a compound of formula I or a pharmaceutically acceptable acid addition salt thereof. An effective dose ranges from about 0.1 to about 15 mg/kg of body weight with a dosage dependent on effects sought, manner of administration, and to some extent with the particular compound selected. Systemic administration refers to oral, rectal, and parenteral (i.e. intramuscular, intravenous and subcutaneous). Generally, it will be found that when a compound of the present invention is administered orally, a larger quantity of the active agent is required to produce the same effect as a smaller quantity given parenterally. In accordance with good clinical practice, it is preferred to administer the instant compounds at a concentration which will produce the desired level of tranquilization and analgesic and antidepressant effects without causing any harmful or untoward side effects.

The compounds of the present invention may be administered for these purposes either as individual therapeutic agents or mixtures with other therapeutic agents. Therapeutically. they are generally given as pharmaceutical compositions comprised of a tranquilizing amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs and aqueous solutions.

The nature of the pharmaceutical composition employed will, of course, depend on the desired route of administration. For example. oral compositions may be in the form of tablets or capsules and may contain conventional excipients such as binding agent (e.g. syrup. acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethyleneglycol or silica), disintegrants (e.g. starch) and wetting agents (e.g. sodium lauryl sulfate). Solutions or suspensions of a Formula I compound with conventional pharmaceutical vehicles are employed for parenteral composition such as an aqueous solution for intravenous injection or an oily suspension for intramuscular injection.

DESCRIPTION OF THE SPECIFIC EMBODIMENT

The compounds which constitute this invention and their methods of preparation will appear more fully from a consideration of the following examples which are given for the purpose of illustration only and are not to be construed as limiting invention in sphere or scope. All temperatures are understood to be in degrees C when not specified. In addition to the elemental analysis data which is given, spectra of the compounds was consistent with their assigned structure.

EXAMPLE 1

4-(3-Chlorophenyl)piperazine-1-butyronitrile (III)

A mixture of 4-(3-chlorophenyl)piperazine (IV, 24.37 g, 0.124 mol), 4-chlorobutyronitrile (V, 16.0 g, 0.157 mol) and pulverized $K_2CO_3$(21.0 g. 0.154 mol) in MeCN (100 mL) was stirred and heated under reflux overnight. The hot reaction was filtered, the filtrate concentrated in vacuo and the residue partitioned between water and $CHCl_3$. The organic layer was dried ($MgSO_4$) and concentrated in vacuo to afford 22.6 g (69%) of crude nitrile as an orange oil which was used without further purification.

EXAMPLE 2

5-[3-[4-(3-Chlorophenyl)-1-piperazinyl]propyl]-1H-tetrazole (II)

A mixture of the nitrile III, (22.6 g. 0.098 mol), $NaN_3$(6.36 g, 0.098 mol) and $NH_4Cl$(5.28 g, 0.098 mol) in dry DMF (65 mL) was magnetically stirred and heated at 140° C. overnight. The cooled reaction mixture was diluted with 65 mL water and extracted with $CHCl_3$; the dried ($MgSO_4$) extract was concentrated in vacuo to a viscous oil which solidified upon standing to afford 4.5 g of a pinkish solid. The $CHCl_3$-extracted aqueous phase was neutralized with glacial HOAc (5.9 g) and re-extracted with $CHCl_3$. The dried extract was concentrated to afford an additional 2.8 g of crude product. The crude solid fractions were combined and recrystallized from EtOH-iPrOH to provide 5.43 g (18%) of tetrazole (II) as an off-white solid. mp 162°-164° C. Anal. calculated for $C_{14}H_{19}ClN_6$: C, 54.81; H, 6.24; N, 27.39. Found: C, 54.76; H, 6.28; N, 27.64.

EXAMPLE 3

1-(3-Chlorophenyl)-4-[3-[5-(trifluoromethyl)-1,3,4-oxadiazol-2-yl]propyl]piperazine hydrochloride (I)

A mixture of the tetrazole II (2.5 g. 0.008 mol) in trifluoroacetic anhydride (15 mL) was heated under reflux for 3h then concentrated in vacuo. The residue was partitioned between 0.5N NaOH and $CHCl_3$, the organic layer shaken with several additional portions of 0.5N NaOH and saturated NaCl solution, dried ($MgSO_4$) and concentrated to 2.8 g of a viscous amber oil. A solution of the latter in dry THF was treated with ethanolic HCl, diluted with ether and refrigerated. The precipitated salt was collected by filtration and recrystallized from iPrOH to afford 2.37 g (72%) of product I as a white solid, mp 151°-153° C.

Anal. calculated for $C_{16}H_{18}ClF_3N_4O.HCl$:C,b 46.73; H,4.66; N, 13.63. Found: C, 46.87; H, 4.67; N, 13.42.

EXAMPLE 4

1-(3-Chlorophenyl)-4-[3-(5-methyl-1,3,4-oxadiazol-2-yl)propyl]piperazine hydrochloride 2-propanolate (I)

A mixture of tetrazole II (6.0 g. 0.0195 mol) in acetic anhydride (24 mL) was heated at 110° C. for 2h. poured into 150 mL water and the aqueous mixture was basified with 50% NaOH and extracted with $CHCl_3$. The extract was shaken with saturated NaCl solution, dried ($MgSO_4$) and concentrated to 4.5 g of a viscous amber oil. The latter was flash-chromatographed on silica gel using ETOAc-MeOH (4%) as eluant. Fractions containing a single component of $R_f$0.56 (silica gel. $CHCl_3$-MeOH (10%) were pooled and concentrated in vacuo to give 3.6 g (58%) of the free base as a viscous orange oil. A portion (1.64 g) of the oil in 3 mL dry THF was treated with ethanolic HCl, diluted with ether and refrigerated. The precipitated salt was collected by filtration and recrstallized from iPrOH to provide 1.66 g of product I as a white solid, mp 124°-126° C. Anal. calculated for $C_{16}H_{21}ClN_4O.HCl.0.5C_3H_8O$: C, 54.27; H, 6.77: N. 14.47. Found: C, 54.33; H, 6.69: N, 14.68.

What is claimed:

1. A compound of Formula I

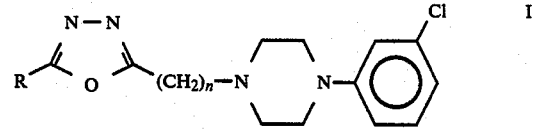

and its pharmaceutically acceptable acid-addition salts wherein

R is $C_{1-4}$ alkyl, trifluoromethyl or pentafluoroethyl; and n is the integer 3 or 4.

2. A compound of claim 1 wherein n is 3.

3. A compound of claim 1 wherein R is methyl.

4. A compound of claim 1 wherein R is trifluoromethyl.

5. The compound of claim 3, 1-(3-chlorophenyl)-4-[3-(5-methyl-1,3,4-oxadiazol-2-yl)propyl]piperazine.

6. The compound of claim 4, 1-(3-chlorophenyl)-4-[3-(5-trifluoromethyl-1,3,4-oxadiazol-2-yl)propyl]piperazine.

7. The method of tranquilizing a mammal in need of such treatment which comprises administration to said mammal of a therapeutically effective tranquilizing amount of a compound of claim 1.

8. The method of providing analgesia for a mammal in need of such treatment which comprises administration to said mammal of a therapeutically effective analgesic amount of a compound of claim 1.

9. The method of alleviating depression in a mammal in need of such treatment which comprises administering to said mammal a therapeutically effective antidepressant amount of a compound of claim 1.

10. The pharmaceutical composition comprising a tranquilizing, analgesic or antidepressant amount of compound of claim 1 and a pharmaceutically acceptable carrier.

* * * * *